United States Patent [19]

Schwartz

[11] Patent Number: 4,791,684
[45] Date of Patent: Dec. 20, 1988

[54] EAR HELD EARMUFF

[76] Inventor: Arnold Schwartz, 226-26 Union Turnpike, Bayside, N.Y. 11364

[21] Appl. No.: 116,915

[22] Filed: Nov. 5, 1987

[51] Int. Cl.⁴ ............................................. A41D 21/00
[52] U.S. Cl. ........................................................ 2/209
[58] Field of Search ........................... 2/209, 174, 423; 381/68, 187, 68.7; 379/430

[56] References Cited

U.S. PATENT DOCUMENTS

| | | | |
|---|---|---|---|
| 190,720 | 5/1877 | Kleinert | 2/209 |
| 2,712,134 | 7/1955 | Cyr | 2/209 |
| 2,727,245 | 12/1955 | Suggs | 2/174 |
| 2,768,384 | 10/1956 | Crane et al. | 2/209 X |
| 4,669,129 | 6/1987 | Chance | 2/209 |

Primary Examiner—Peter Nerbun
Attorney, Agent, or Firm—Michael I. Kroll

[57] ABSTRACT

An ear held earmuff is provided and consists of an inner securement member placed over helix of outer ear of a person and an outer muff member sized to cover the outer ear of the person which is removably attached to the inner securement member to protect the outer ear of the person against the cold weather.

5 Claims, 1 Drawing Sheet

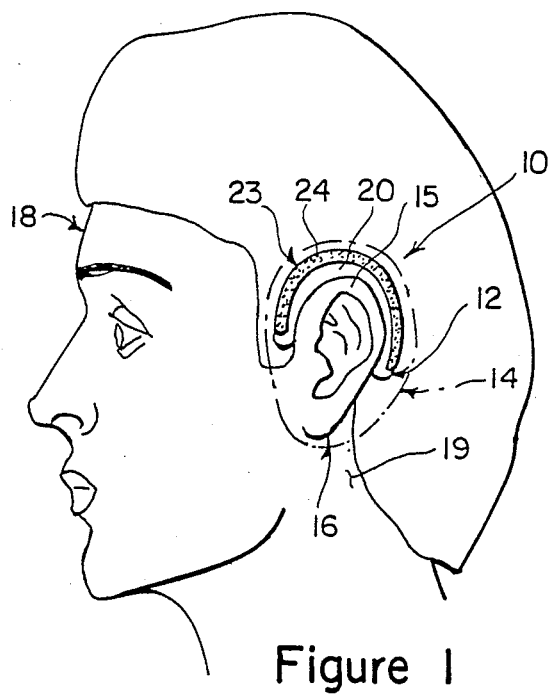
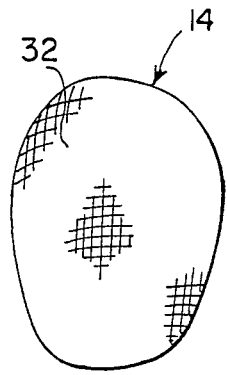
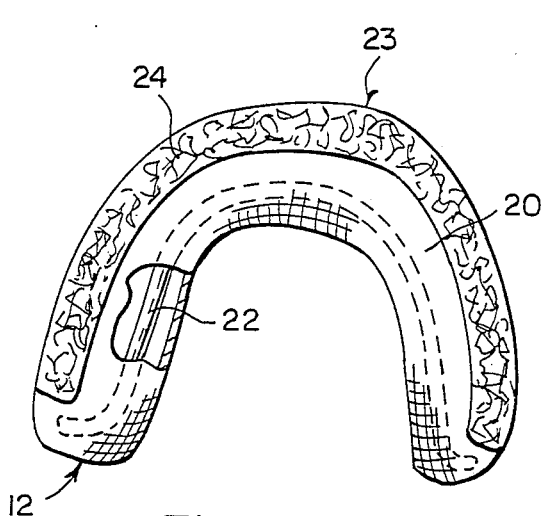
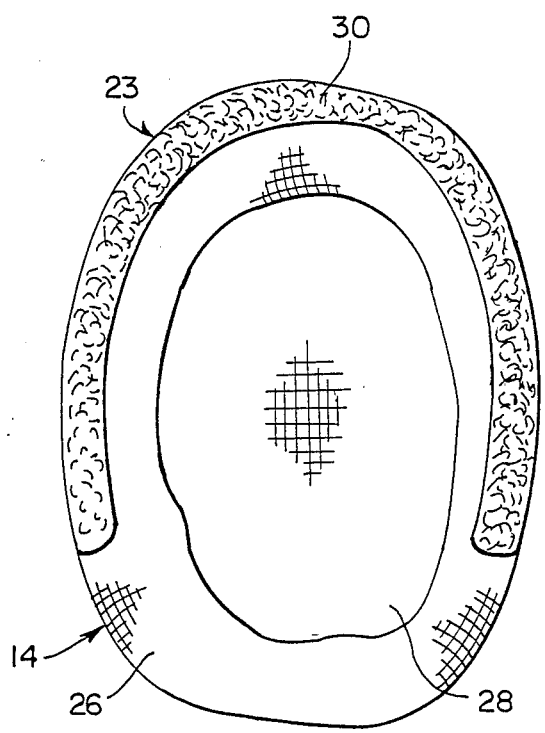
Figure 1
Figure 2
Figure 3
Figure 4

EAR HELD EARMUFF

BACKGROUND OF THE INVENTION

1. Field of the Invention

The instant invention relates generally to ear coverings and more specifically it relates to an ear held earmuff held to the ear by a fastener.

2. Description of the Prior Art

Numerous ear coverings have been provided in prior art that are adapted to include a pair of earmuffs attached to an adjustable headband and worn to protect against the cold. While these units may be suitable for the particular purpose to which they address, they would not be as suitable for the purposes of the present invention as heretofore described.

SUMMARY OF THE INVENTION

A primary object of the present invention is to provide an ear held earmuff that will overcome the shortcomings of the prior art devices.

Another object is to provide an ear held earmuff that will fit more comfortably to the outer ear of a person.

An additional object is to provide an ear held earmuff that will eliminate the need for the adjustable headband worn on the head of the person.

A further object is to provide an ear held earmuff that is simple and easy to use.

A still further object is to provide an ear held earmuff that is economical in cost to manufacture.

Further object of the invention will appear as the description proceeds.

To the accomplishment of the above and related objects, this invention may be embodied in the fore illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

FIG. 1 is a side view of a person's head with inner securement member placed over helix of the outer ear with outer muff member shown in phanton thereon.

FIG. 2 is an enlarged elevational view with parts broken away of the inner securement members showing construction thereof.

FIG. 3 is an enlarged rear view of the outer muff member.

FIG. 4 is a front view of the outer muff member.

DETAILED DESCRIPTION OF THE PREFERRED EMBODIMENTS

Turning now descriptively to the drawings, in which similar reference characters denote similar elements throughout the several views, FIG. 1 illustrates an ear held earmuff 10 that consists of an inner securement member 12 placed over helix 15 of outer ear 16 of a person 18, an outer muff member 14 sized to cover the outer ear 16 of the person and a fastener 23 for removably attaching the outer muff member 14 to the inner securement member 12 to protect the outer ear 16 of the person 18 against the cold weather.

As best seen in FIG. 2, the inner securement member 12 includes an elongated length of pliable wire 22 and a soft thick piece of plush material 20, covering the pliable wire 22 so that the pliable wire 22 can be bent, with the piece of plush material 20 to fit between the helix 15 of the outer ear 16 and skull 19 of the person 18 thereby biasing the outer ear away from the skull due to the thickness of the plush material.

As best seen in FIGS. 3 and 4, the outer muff member 14 includes piece of plush soft material 32 folded over into an oval shape that has a ring 26 therearound with a cavity inner face 28 to cover the outer ear 16 of the person 18.

The fastener 23 includes two strips 24 and 30 of adhering material. One of the strips 24 is attached to the piece of plush material 20 of the inner securement member 12 and other of the strips 30 is attached to upper portion of the ring 26 of the piece of plush soft material 32 of the outer muff member 14. When the outer muff member 14 is placed against the inner securement member 12, the outer muff member will be held thereto. The two strips 24 and 30 of adhering material shown in FIGS. 1, 2 and 3 are a pair of hook and loop pile fabric fastener strips, but other types of fasteners, such as adhesive strips, slide fasteners, snaps, etc., (not shown) can be utilized to accomplish the same results.

It will be understood that each of the elements described above, or two or more together, may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. An ear held earmuff which comprises:
   (a) an outer muff member sized to cover the outer ear of a person;
   (b) a thick inner securement member removably attached to said outer muff member and placed over the helix of an outer ear of a person so as to bias the outer ear of the person away from the skull of the person and be held between the outer ear of the person and the skull of the person so that the ear held earmuff is more securely fitted to the person; and
   (c) means for removably attaching said outer muff member to said inner securement member to protect the outer ear of the person against the cold weather.

2. An ear held earmuff as recited in claim 1, wherein said inner securement member includes:
   (a) an elongated length of pliable wire; and
   (b) a soft thick piece of plush material, covering the said pliable wire so that said pliable wire can be bent.

3. An ear held earmuff as recited in claim 2, wherein said outer muff member includes a piece of plush soft material folded over into an oval shape having a ring therearound with a cavity inner face to cover the outer ear of the person.

4. An ear held earmuff as recited in claim 3, wherein the removable attaching means includes two strips of adhering material, one of said strips attached to said piece of plush material of said inner securement member and other of said strips attached to an upper portion of the ring of said piece of plush soft material of said outer muff member so that when said outer muff member is placed against said inner securement member said outer muff member will be held thereto.

5. An ear held earmuff as recited in claim 4, wherein said two strips of adhering material are a pair of hook and loop pile fabric fastener strips.

* * * * *